(12) United States Patent
Heddesheimer et al.

(10) Patent No.: US 8,378,113 B2
(45) Date of Patent: Feb. 19, 2013

(54) PROCESS FOR THE MANUFACTURE OF AN INTERMEDIATE IN THE SYNTHESIS OF DABIGATRAN

(75) Inventors: Ingo Heddesheimer, Monzingen (DE); Ulrich Scholz, Bad Kreuznach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 195 days.

(21) Appl. No.: 12/997,349

(22) PCT Filed: Jun. 12, 2009

(86) PCT No.: PCT/EP2009/057265
§ 371 (c)(1),
(2), (4) Date: Feb. 4, 2011

(87) PCT Pub. No.: WO2009/153214
PCT Pub. Date: Dec. 23, 2009

(65) Prior Publication Data
US 2011/0295018 A1     Dec. 1, 2011

(30) Foreign Application Priority Data
Jun. 16, 2008    (EP) .................................. 08158363

(51) Int. Cl.
*C07D 213/75*     (2006.01)
(52) U.S. Cl. ...................................... 546/309
(58) Field of Classification Search ......... None
See application file for complete search history.

(56) References Cited

FOREIGN PATENT DOCUMENTS
WO    2007/071743 A1    6/2007

OTHER PUBLICATIONS

Hauel, Norbert H., et al; Structure-Based Design of Novel Potent Nonpeptide Thrombin Inhibitors; Journal of Medicinal Chemistry (2002) vol. 45, No. 9 pp. 1757-1766.
International Search Report for PCT/EP2009/057265 mailed Aug. 6, 2009.

*Primary Examiner* — Zinna Northington Davis
(74) *Attorney, Agent, or Firm* — Michael P. Morris; Wendy A. Petka

(57) ABSTRACT

The invention relates to a process for the synthesis of the diamine of formula (1) an important intermediate in the synthesis of dabiagtran etexilate.

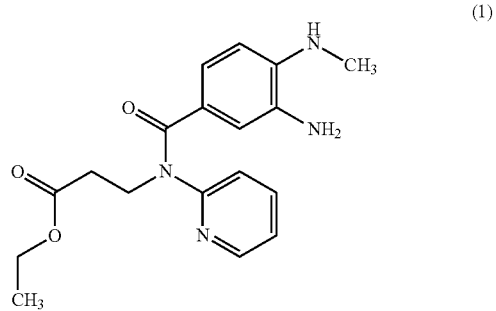

(1)

6 Claims, No Drawings

PROCESS FOR THE MANUFACTURE OF AN INTERMEDIATE IN THE SYNTHESIS OF DABIGATRAN

This application is the national phase entry under 35 U.S.C. §371 of International Application No. PCT/EP2009/057265, filed Jun. 12, 2009, which claims priority to European Patent Application No. 08158363.5, filed Jun. 16, 2008, the contents of which are hereby incorporated by reference in their entireties.

The invention relates to a process for the synthesis of the diamine of formula 1

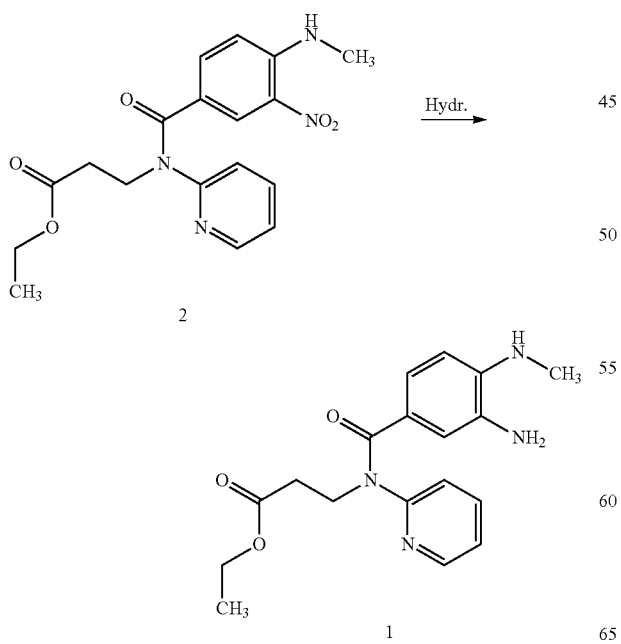

an important intermediate in the synthesis of dabiagtran etexilate.

BACKGROUND OF THE INVENTION

Dabigatrane etexilate is known in the art and was first disclosed in International patent application WO 98/37075. Processes for the manufacture of dabigatran etexilate are also known from WO 2006/000353 or Hauel et al. (J. Med. Chem, 2002, 45, 1757 ff).

According to Hauel et al 1 can be obtained from nitrocompound of formula 2 via hydrogenation on Pd/C.

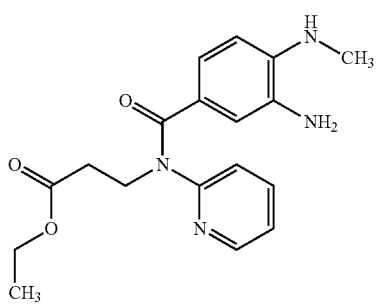

However, in particular in large-scale processes the reaction occasionally stops due to catalyst poisoning which leads to an incomplete turnover of the starting material. This can require further addition of catalyst during the course of the reaction. Moreover, reaction time is prolonged which has a negative influence on the quality of the reaction product 1. The process for manufacture of 2 is for instance disclosed in Hauel et al (J. Med. Chem, 2002, 45, 1757-1766). From the synthesis of 2 as disclosed in Hauel et al., it is apparent that process related sulfur impurities might be carried over into 2 with varying amounts. These impurities strongly influence the reaction time, quality and catalyst consumption in the manufacture of 1.

Therefore, it is the object of the invention to provide for an improved process for the manufacture of 1 which overcomes the foregoing deficiencies that are associated with catalyst poisoning.

DESCRIPTION OF THE INVENTION

Surprisingly, it has been found that the problem underlying the invention can be solved by the addition of tertiary amine to the reaction mixture.

Consequently, the invention relates to the synthesis of compound of formula 1

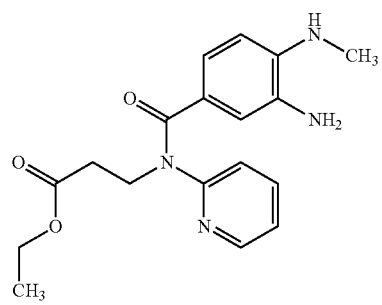

through catalytic hydrogenation of compound of formula 2

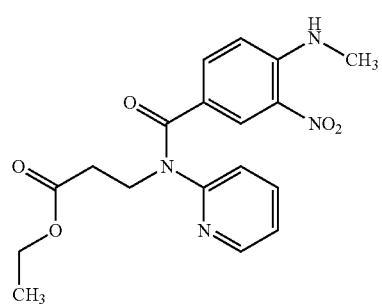

characterized in that the reaction is conducted in the presence of a tertiary amine.

In a particularly preferred process, the hydrogenation is carried out in a temperature range from 0° C. to 100° C., preferably from 10° C. to 80° C., particularly from 20° C. to 60° C. Also preferred is a process wherein the hydrogenation is carried out under a pressure of more than 0.5 bar to 25 bar, preferably under a pressure of 1 bar to 8 bar, particularly at about 2-6 bar.

The solvents preferably used within the process according to the invention may be both protic solvents—such as e.g. alcohols, carboxylic acids and/or water—or aprotic polar solvents such as e.g. ethers, esters, amides or lactams and/or mixtures thereof. Water may optionally be added to all the solvents. Preferred protic solvents used are branched or unbranched $C_1$-$C_8$ alkanols, $C_1$-$C_3$ carboxylic acids or mixtures thereof. Particularly preferably, lower alcohols such as methanol, ethanol, n-propanol and isopropanol, carboxylic acids such as formic acid, acetic acid and propionic acid or mixtures thereof are used. Preferred aprotic solvents are polar ethers such as for example tetrahydrofuran or dimethoxyethylether, amides such as for example dimethylformamide, lactams such as for example N-methylpyrrolidone or esters like for instance ethyl acetate. Most preferred solvent according to the invention is ethyl acetate.

Suitable hydrogenation catalysts are generally transition metals such as for example nickel, platinum or palladium or the salts or oxides thereof. Raney nickel, platinum oxide and palladium on an inert carrier material, particularly palladium on activated charcoal (Pd/C), are preferred.

The tertiary amine is preferably selected from among trimethylamine, triethylamine, diisopropylethylamine and DBU (diazabicycloundecene). Most preferred amine is triethylamine.

The amount of tertiary amine used within the scope of the invention is based on the amount of starting material 2 in the range of 0.05 to 10%, preferably 0.5-7%, most preferred 2-6%. The foregoing amount is indicated in weight percentage relative to starting material 2.

In the following examples the same compound 2 batch was used as the starting material. Prior to the experiments it was determined that the batch contained about 380 ppm of sulfur impurities.

Example According to the Invention

Under inert atmosphere ($N_2$) an autoclave is charged with 150 g of compound 2, 6 g of a 10% Palladium on Charcoal catalyst, 7 ml of triethylamine and 630 ml of ethyl acetate. The autoclave is heated to 30° C. and hydrogen added until a pressure of 4 bars is observed. Then the temperature is adjusted to 50° C. The usual time for complete conversion of the starting material is 1 to 2 h. The autoclave is then allowed to cool and the suspension filtered to remove the catalyst. The organic filtrate is concentrated on a rotary evaporator and diluted with 350 ml of either isopropanol or toluene. Again the solution is concentrated using mild vacuum and 400 ml of either isopropanol or toluene are added. The solution is cooled to 10° C. to allow crystallisation of the product. The crude product is isolated by filtration and dried under vacuum to yield 123 g (90% of theoretical yield) of compound 1.

Reference Example (Prior Art)

Under inert atmosphere ($N_2$) an autoclave is charged with 150 g of compound 2, 6 g of a 10% Palladium on Charcoal catalyst and 630 ml of Ethyl acetate. The autoclave is heated to 30° C. and Hydrogen added until a pressure of 4 bars is observed. Then the temperature is adjusted to 50° C. If hydrogen uptake ceases or is slow, the autoclave is flushed with nitrogen and additional catalyst is added (appr. 50% of the original amount), then new hydrogen is added and hydrogenation continued. The usual time for complete conversion of the starting material is approximately 4 hours. The autoclave is then allowed to cool and the suspension filtered to remove the catalyst. The organic filtrate is concentrated on a rotary evaporator and diluted with 350 ml of either isopropanol or toluene. Again the solution is concentrated using mild vacuum and 400 ml of either isopropanol or toluene are added. The solution is cooled to 10° C. to allow crystallisation of the product. The crude product is isolated by filtration and dried under vacuum to yield 116 g (85% of theoretical yield) of 1.

The invention claimed is:

1. A process for the synthesis of a compound of formula 1

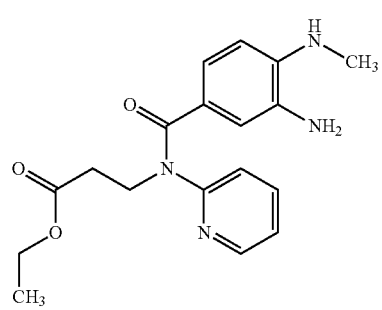

comprising the step of catalytically hydrogenating a compound of formula 2

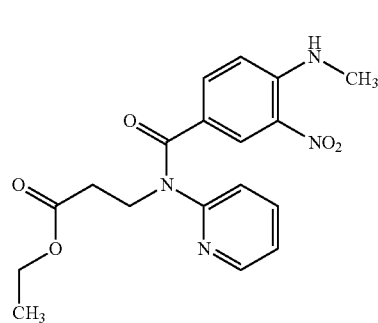

wherein the reaction is conducted in the presence of a tertiary amine.

2. The process according to claim 1, wherein the tertiary amine is selected from among trimethylamine, triethylamine, diisopropylethylamine and DBU (diazabicycloundecene).

3. The process according to claim 1 or 2, wherein the hydrogenation step is carried out in a temperature range from 0° C. to 100° C.

4. The process according to claim 1 or 2 further comprising a solvent selected from branched or unbranched $C_1$-$C_8$ alkanols, $C_1$-$C_3$ carboxylic acids, polar ethers, amides and esters.

5. The process according to claim 3, wherein the hydrogenation step is carried out in a temperature range from 10° C. to 80° C.

6. The process according to claim 5, wherein the hydrogenation step is carried out in a temperature range from 20° C. to 60° C.

* * * * *